(12) United States Patent
Zhou et al.

(10) Patent No.: US 9,828,455 B2
(45) Date of Patent: *Nov. 28, 2017

(54) STYRENE-BUTADIENE BLOCK COPOLYMERS WITH AN INTERNAL BUTADIENE BLOCK FOR TUBING APPLICATIONS

(71) Applicant: INEOS STYROLUTION GROUP GMBH, Frankfurt am Main (DE)

(72) Inventors: Jinping Joe Zhou, Bartlesville, OK (US); Walter H. Pace, Bartlesville, OK (US); David A. Young, Caney, KS (US)

(73) Assignee: INEOS STYROLUTION GROUP GMBH (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/051,807

(22) Filed: Feb. 24, 2016

(65) Prior Publication Data

US 2017/0240678 A1 Aug. 24, 2017

(51) Int. Cl.
*C08L 53/02* (2006.01)
*C08F 297/02* (2006.01)
*C08F 293/00* (2006.01)

(52) U.S. Cl.
CPC .......... *C08F 293/005* (2013.01); *C08L 53/02* (2013.01)

(58) Field of Classification Search
CPC ............................ C08F 293/005; C08L 53/02
See application file for complete search history.

(56) References Cited

U.S. PATENT DOCUMENTS

| | | | |
|---|---|---|---|
| 3,639,517 A | 2/1972 | Kitchen et al. | |
| 3,855,189 A | 12/1974 | Farrar et al. | |
| 3,865,776 A | 2/1975 | Gergen | |
| 4,048,254 A | 9/1977 | Hillier et al. | |
| 4,067,942 A | 1/1978 | Wilson | |
| 4,086,298 A | 4/1978 | Fahrbach et al. | |
| 4,088,813 A | 5/1978 | Willis | |
| 4,091,053 A | 5/1978 | Kitchen | |
| 4,386,190 A | 5/1983 | Bailey | |
| 4,403,074 A | 9/1983 | Moczygemba | |
| 4,405,754 A | 9/1983 | Moczygemba et al. | |
| 4,418,180 A | 11/1983 | Heinz et al. | |
| 4,440,815 A | 4/1984 | Zomorodi et al. | |
| 4,615,851 A | 10/1986 | Theodore et al. | |
| H179 H | 12/1986 | Klingensmith et al. | |
| 4,631,314 A | 12/1986 | Tung et al. | |
| 4,704,434 A | 11/1987 | Kitchen et al. | |
| 5,001,009 A | 3/1991 | Whitbourne | |
| 5,130,377 A | 7/1992 | Trepka et al. | |
| 5,198,495 A | 3/1993 | Fasulo et al. | |
| 5,227,419 A | 7/1993 | Moczygemba et al. | |
| 5,256,736 A | 10/1993 | Trepka et al. | |
| 5,274,035 A | 12/1993 | Chundury | |
| 5,290,875 A | 3/1994 | Moczygemba et al. | |
| 5,319,033 A | 6/1994 | Trepka et al. | |
| 5,331,048 A | 7/1994 | Hasselbring | |
| 5,369,174 A | 11/1994 | Hasselbring | |
| 5,393,838 A | 2/1995 | Moczygemba et al. | |
| 5,399,628 A | 3/1995 | Moczygemba et al. | |
| 5,436,298 A | 7/1995 | Moczygemba et al. | |
| 5,438,103 A | 8/1995 | DePorter et al. | |
| 5,545,690 A | 8/1996 | Trepka et al. | |
| 5,587,425 A | 12/1996 | Moczygemba et al. | |
| 5,705,569 A | 1/1998 | Moczygemba et al. | |
| 5,854,353 A | 12/1998 | Knoll et al. | |
| 5,885,530 A | 3/1999 | Babson et al. | |
| 5,910,546 A | 6/1999 | Trepka et al. | |
| 6,096,828 A | 8/2000 | DePorter et al. | |
| 6,107,411 A | 8/2000 | Toya et al. | |
| 6,197,889 B1 | 3/2001 | Knoll et al. | |
| 6,238,408 B1 | 5/2001 | Kawabata et al. | |
| 6,239,218 B1 | 5/2001 | Yonezawa et al. | |
| 6,265,484 B1 | 7/2001 | Trepka et al. | |
| 6,265,485 B1 | 7/2001 | Trepka et al. | |
| 6,420,486 B1 | 7/2002 | DePorter et al. | |
| 6,444,755 B1 | 9/2002 | DePorter et al. | |
| 6,521,712 B1 | 2/2003 | Knoll et al. | |
| 6,548,181 B2 | 4/2003 | Beusen | |
| 6,593,430 B1 | 7/2003 | Knoll et al. | |
| 6,835,778 B2 | 12/2004 | Swisher et al. | |
| 6,841,261 B2 | 1/2005 | Matsui et al. | |
| 6,846,535 B2 | 1/2005 | De Groot et al. | |
| 7,037,980 B2 | 5/2006 | Stacy et al. | |
| 7,067,589 B2 | 6/2006 | Bening et al. | |

(Continued)

FOREIGN PATENT DOCUMENTS

| | | |
|---|---|---|
| DE | 1 491 741 | 11/1977 |
| EP | 0 512 530 | 11/1992 |

(Continued)

OTHER PUBLICATIONS

International Search Report and the Written Opinion of the International Searching Authority in PCT/US2016/021948 dated Jun. 9, 2016, 8 pages.
U.S. Appl. No. 15/226,945, filed Aug. 3, 2016, entitled "Styrene-Butadiene Block Copolymers with an Internal Butadiene Block for Tubing Applications."
CEN European Standard, "Test methods for kinking of single lumen catheters and medical tubing," EN 13868 (2002), 13 pages.
Hsieh, Henry L et al., "Kinetics of Alkyllithium Initiated Polymerizations," Rubber Chemistry and Technology, (1970), 43(1 ), pp. 22-73.
International Search Report and the Written Opinion of the International Searching Authority in PCT/US2016/021919 dated May 19, 2016, 8 pages.
Kennedy et al., "Synthesis and Characterisation of Styrene Butadiene Styrene Based Grafted Copolymers for Use in Potential Biomedical Application;" Biomedical Engineering, Trends in Materials Science, Department of Polymer Engineering, Athlone Institute of Technology, Ireland, www.intechopen.com; (2001) pp. 465-488.

(Continued)

Primary Examiner — Jeffrey Mullis
(74) Attorney, Agent, or Firm — J.A. Lindeman & Co., PLLC

(57) ABSTRACT

Conjugated diene monovinylarene block copolymers containing an internal conjugated diene block and having superior kink resistance properties are disclosed. These copolymers can be used to produce tubing and other end-use articles, and can be a replacement for flexible PVC.

25 Claims, 1 Drawing Sheet

(56) References Cited

U.S. PATENT DOCUMENTS

| | | |
|---|---|---|
| 7,138,456 B2 | 11/2006 | Bening et al. |
| 7,169,848 B2 | 1/2007 | Bening et al. |
| 7,169,850 B2 | 1/2007 | Handlin, Jr. et al. |
| 7,193,014 B2 | 3/2007 | Wilkey et al. |
| 7,332,542 B2 | 2/2008 | Bening et al. |
| 7,700,688 B2 | 4/2010 | Uzee et al. |
| 7,737,216 B2 | 6/2010 | Brown et al. |
| 7,776,965 B2 | 8/2010 | Wilkey et al. |
| 7,875,678 B2 | 1/2011 | Hanner et al. |
| 8,058,346 B2 | 11/2011 | Wilkey et al. |
| 8,236,894 B2 | 8/2012 | Brown et al. |
| 8,415,429 B2 | 4/2013 | Brown et al. |
| 8,933,171 B2 | 1/2015 | Pettey et al. |
| 9,040,628 B2 | 5/2015 | Brown et al. |
| 9,174,377 B2 | 11/2015 | Pettey et al. |
| 9,441,090 B1 | 9/2016 | Zhou |
| 2002/0002363 A1 | 1/2002 | Urakawa et al. |
| 2002/0061982 A1 | 5/2002 | Donald et al. |
| 2003/0004267 A1 | 1/2003 | Swisher et al. |
| 2003/0144418 A1 | 7/2003 | Donald et al. |
| 2004/0072956 A1 | 4/2004 | Degroot et al. |
| 2004/0115381 A1 | 6/2004 | Harris et al. |
| 2006/0089457 A1 | 4/2006 | Hartsock et al. |
| 2006/0100386 A1 | 5/2006 | Wilkey et al. |
| 2006/0211818 A1 | 9/2006 | Kurimura et al. |
| 2006/0235118 A1 | 10/2006 | Shelby et al. |
| 2006/0235188 A1 | 10/2006 | Weinhold et al. |
| 2007/0027257 A1 | 2/2007 | Kobashi et al. |
| 2007/0043168 A1 | 2/2007 | Montiel-Ortiz et al. |
| 2007/0093601 A1 | 4/2007 | Watanabe et al. |
| 2007/0173605 A1 | 7/2007 | Brown et al. |
| 2008/0215016 A1 | 9/2008 | Igarashi et al. |
| 2011/0098401 A1 | 4/2011 | Müller et al. |
| 2011/0251596 A1 | 10/2011 | Kim et al. |
| 2011/0319837 A1 | 12/2011 | Uehara et al. |
| 2012/0270979 A1 | 10/2012 | Hsu et al. |
| 2013/0079471 A1 | 3/2013 | Brown |
| 2016/0264705 A1 | 9/2016 | Zhou et al. |
| 2016/0264773 A1 | 9/2016 | Zhou et al. |

FOREIGN PATENT DOCUMENTS

| | | |
|---|---|---|
| EP | 0 553 689 | 8/1993 |
| EP | 0 603 852 | 6/1994 |
| EP | 0 646 607 | 4/1995 |
| EP | 0 654 488 | 5/1995 |
| EP | 0 761 704 | 3/1997 |
| EP | 1 123 715 | 8/2001 |
| EP | 1 605 002 | 12/2005 |
| EP | 2 186 859 | 5/2010 |
| EP | 2 407 512 | 1/2012 |
| JP | 2006/083233 | 3/2006 |
| WO | WO 01/94466 | 2/2001 |
| WO | WO 01/25303 | 4/2001 |
| WO | WO 03/018685 | 3/2003 |

OTHER PUBLICATIONS

Knoll, Konrad et al. "Styrolux and styroflex. From Transparent High Impact Polystyrene to New Thermoplastic Elastomers. Syntheses, Applications, and Blends with Other Styrene-Based Polymers," Macromolecular Symposia (1998), 132, pp. 231-243.

Kraus, Gerald et al., "Morphology and Dynamic Viscoelastic behavior of blends of Styrene-Butadiene Block Copolymers," Adv. Chem. Ser., (1979), 176, pp. 277-292.

U.S. Appl. No. 14/645,658, filed Mar. 12, 2015, entitled "Styrene-Butadiene Block Copolymers for Tubing Applications."

U.S. Appl. No. 14/645,841, filed Mar. 12, 2015, entitled "Methods for Controlling Hardness of Styrene-Butadiene Block Copolymers."

U.S. Appl. No. 14/844,039, filed Sep. 3, 2015, entitled "Blends of Styrene-Butadiene Block Copolymer with Styrenic Thermoplastic Elastomers for Tubing Applications."

U.S. Appl. No. 14/857,875, filed Sep. 18, 2015, entitled "Styrene-Butadiene Block Copolymers With a Terminal Butadiene Block for Tubing Applications."

U.S. Appl. No. 15/067,234, filed Mar. 11, 2016, entitled "Styrene-Butadiene Block Copolymers for Tubing Applications."

International Search Report and Written Opinion in International Application No. PCT/US2016/067098, dated Mar. 9, 2017.

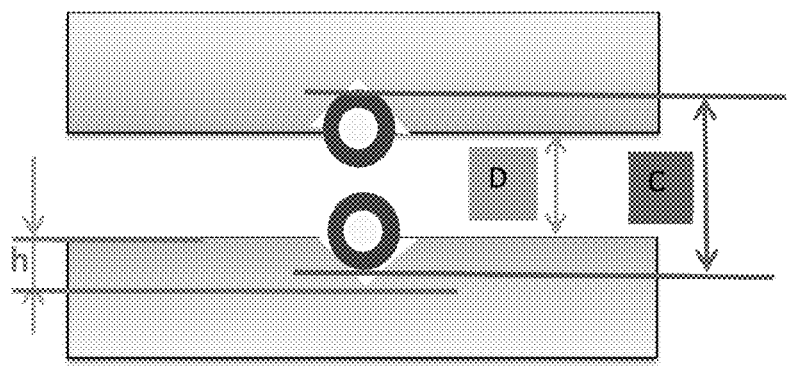

STYRENE-BUTADIENE BLOCK COPOLYMERS WITH AN INTERNAL BUTADIENE BLOCK FOR TUBING APPLICATIONS

BACKGROUND OF THE INVENTION

Flexible PVC has been the material of choice for many applications due to its low cost and unique combination of properties. In applications such as flexible tubing for medical applications, flexible PVC has suitable strength, flexibility, and kink resistance, and yet is not too tacky or sticky. However, flexible PVC requires significant amounts of plasticizers, which depending upon the specific composition, are being replaced or phased out due to health concerns and PVC incineration by-product concerns.

It would be beneficial to have a non-PVC composition that has acceptable strength and flexibility, reduced tackiness, and improved kink resistance for use in medical tubing and other traditional PVC applications. Accordingly, it is to these ends that the present invention is directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Conjugated diene monovinylarene block copolymers are disclosed and described herein, and such copolymers can comprise from about 35 phm to about 75 phm monovinylarene monomer (phm is the parts by weight per hundred parts of total monomer in the copolymer), and moreover, can comprise polymer chains containing a block structure having formula IA or formula IB:

In formula IA and IB, $S_1$ can be a monoblock of the monovinylarene monomer, wherein $S_1$ can be from about 15 phm to about 45 phm of the copolymer; $B_1$ can be a first monoblock of the conjugated diene monomer, wherein $B_1$ can be from about 0.5 phm to about 10 phm of the copolymer; $(S/B)_1$ can be a mixed block of the conjugated diene monomer and the monovinylarene monomer, wherein the monovinylarene monomer content can be from about 30 wt. % to about 80 wt. %, based on the total weight of $(S/B)_1$; $(S/B)_2$ can be a mixed block of the conjugated diene monomer and the monovinylarene monomer, wherein the conjugated diene monomer content can be from about 70 wt. % to about 99 wt. %, based on the total weight of $(S/B)_2$; and $B_2$ can be a second monoblock of the conjugated diene monomer, wherein $B_2$ can be from about 8 phm to about 30 phm of the copolymer. The copolymer can be further characterized by a kink resistance of tubing produced from the copolymer of less than or equal to about 32 mm, when tested in accordance with DIN EN 13868.

In one embodiment of this invention, the copolymer can contain polymer chains having the block structure of formula IA, and can have the following characteristics: a monovinylarene monomer content in a range from about 54 phm to about 68 phm, $S_1$ in a range from about 28 phm to about 38 phm, $B_1$ in a range from about 2 phm to about 8 phm, a monovinylarene monomer content in $(S/B)_1$ in a range from about 50 wt. % to about 65 wt. %, and a conjugated diene monomer content in $(S/B)_2$ in a range from about 75 wt. % to about 95 wt. %.

In another embodiment of this invention, the copolymer can contain polymer chains having the block structure of formula IB, and can have the following characteristics: a monovinylarene monomer content in a range from about 54 phm to about 68 phm, $S_1$ in a range from about 28 phm to about 38 phm, $B_1$ in a range from about 2 phm to about 8 phm, a monovinylarene monomer content in $(S/B)_1$ in a range from about 50 wt. % to about 65 wt. %, and $B_2$ in a range from about 14 phm to about 20 phm.

In further embodiments, the copolymer also can comprise polymer chains containing a block structure having formula IIA or formula IIB:

In formula IIA and IIB, $S_2$ can be a monoblock of the monovinylarene monomer, wherein $S_2$ can be from about 5 phm to about 30 phm, or from about 12 phm to about 25 phm. In formula IIA and IIB, each of $B_1$, $(S/B)_1$, $(S/B)_2$, and $B_2$ can be the same as, or different from (e.g., in phm, in relative monovinylarene to conjugated diene content in the mixed block), that described herein for formula IA and IB.

Articles can be produced from and/or can contain the block copolymers (or compositions comprising the block copolymers) disclosed herein. Representative articles can include, but are not limited to, sheet products, film products, tubing products, and adhesive products.

Embodiments of the invention also are directed to methods for producing block copolymers. One such method can comprise contacting (i) a first initiator charge and a first charge of the monovinylarene monomer and allowing polymerization to occur until minimal free monomer is present; thereafter contacting all products of step (i) with (ii) a second initiator charge and a second charge of the monovinylarene monomer and allowing polymerization to occur until minimal free monomer is present; thereafter contacting all products of step (ii) with (iii) a first charge of the conjugated diene monomer and allowing polymerization to occur until minimal free monomer is present; thereafter contacting all products of step (iii) with (iv) a first mixture of the monovinylarene monomer and the conjugated diene monomer and allowing polymerization to occur until minimal free monomer is present; thereafter contacting all products of step (iv) with (v) a second mixture of the monovinylarene monomer and the conjugated diene monomer and allowing polymerization to occur until minimal free monomer is present; thereafter contacting all products of step (v) with (vi) a third mixture of the monovinylarene monomer and the conjugated diene monomer and allowing polymerization to occur until minimal free monomer is present; thereafter contacting all products of step (vi) with (vii) a coupling agent.

Another method for producing a block copolymer consistent with this invention can comprise contacting (i) a first initiator charge and a first charge of the monovinylarene monomer and allowing polymerization to occur until minimal free monomer is present; thereafter contacting all products of step (i) with (ii) a second initiator charge and a second charge of the monovinylarene monomer and allowing polymerization to occur until minimal free monomer is present; thereafter contacting all products of step (ii) with (iii) a first charge of the conjugated diene monomer and allowing polymerization to occur until minimal free monomer is present; thereafter contacting all products of step (iii) with (iv) a first mixture of the monovinylarene monomer and the conjugated diene monomer and allowing polymerization to occur until minimal free monomer is present; thereafter contacting all products of step (iv) with (v) a second mixture of the monovinylarene monomer and the conjugated diene monomer and allowing polymerization to occur until minimal free monomer is present; thereafter contacting all products of step (v) with (vi) a second charge of the conjugated diene monomer and allowing polymerization to occur until minimal free monomer is present; thereafter contacting all products of step (vi) with (vii) a coupling agent.

Both the foregoing summary and the following detailed description provide examples and are explanatory only. Accordingly, the foregoing summary and the following detailed description should not be considered to be restrictive. Further, features or variations may be provided in addition to those set forth herein. For example, certain embodiments may be directed to various feature combinations and sub-combinations described in the detailed description.

BRIEF DESCRIPTION OF THE FIGURE

FIG. 1 presents a schematic of the apparatus used to determine the kink resistance and re-kink resistance of tubing, as described herein.

DEFINITIONS

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

While compositions and methods are described in terms of "comprising" various components or steps, the compositions and methods can also "consist essentially of" or "consist of" the various components or steps, unless stated otherwise. For example, a composition provided in an embodiment of the invention can comprise, or alternatively, consist essentially of, or alternatively, consist of, a block copolymer, a second polymer, and an additive.

The terms "a," "an," and "the" are intended to include plural alternatives, e.g., at least one. For instance, the disclosure of "a conjugated diene monovinylarene block copolymer," "an additive," etc., is meant to encompass one, or mixtures or combinations of more than one conjugated diene monovinylarene block copolymer, additive, etc., unless otherwise specified.

The term "polymer" is used herein generically to include homopolymers, copolymers, terpolymers, and so forth, while a "copolymer" is used generically to include copolymers, terpolymers, and so forth. Thus, "polymer" and "copolymer" encompass polymeric materials derived from any monomer and comonomer (one or more than one) disclosed herein. As would be readily recognized by those of skill in the art, block copolymers in accordance with this invention contain a mixture of polymer chains of various sizes (e.g., a distribution of molecular weights), and the respective polymer chains can vary compositionally (e.g., relative amounts of conjugated diene monomer versus monovinylarene monomer).

As used herein, a "conjugated diene monomer" refers to an organic compound containing conjugated carbon-carbon double bonds and often a total of 4 to 12 carbon atoms, such as from 4 to 8 carbon atoms. Exemplary conjugated diene monomers can include, but are not limited to, 1,3-butadiene, 2-methyl-1,3-butadiene (isoprene), 2-ethyl-1,3-butadiene, 2,3-dimethyl-1,3-butadiene, 1,3-pentadiene, 3-butyl-1,3-octadiene, and the like, as well as mixtures thereof. For example, in some embodiments disclosed herein, the conjugated diene monomer can be a butadiene, while in other embodiments, the conjugated diene monomer can be 1,3-butadiene.

A unit of a polymer, wherein the unit is derived from polymerization of a conjugated diene monomer, can be referred to as a "conjugated diene unit."

As used herein, "monovinylarene monomer" refers to an organic compound containing a single carbon-carbon double bond, at least one aromatic moiety, and often a total of 8 to 18 carbon atoms, such as from 8 to 12 carbon atoms. Exemplary monovinylarene monomers can include, but are not limited to, styrene, alpha-methylstyrene, 2-methylstyrene, 3-methylstyrene, 4-methylstyrene, 2-ethylstyrene, 3-ethylstyrene, 4-ethylstyrene, 4-n-propyl styrene, 4-t-butylstyrene, 2,4-dimethylstyrene, 4-cyclohexylstyrene, 4-decylstyrene, 2-ethyl-4-benzylstyrene, 4-(4-phenyl-n-butyl)styrene, 1-vinylnaphthalene, 2-vinylnaphthalene, diphenylethylene, and the like, as well as mixtures thereof. For example, in some embodiments disclosed herein, the monovinylarene monomer can be styrene.

A unit of a polymer, wherein the unit is derived from polymerization of a monovinylarene monomer, can be referred to as a "monovinylarene unit."

A "conjugated diene monovinylarene block copolymer" is a polymer comprising polymer chains containing monovinylarene monomer units and conjugated diene monomer units. For example, in some embodiments disclosed herein, the conjugated diene monovinylarene block copolymer can be a styrene butadiene copolymer. The conjugated diene monovinylarene block copolymer comprises more than one block, wherein each block comprises monovinylarene monomer units and/or conjugated diene monomer units. If the block comprises only one type of monomer unit, it can be termed a "monoblock." If the block comprises both, it can be termed a "mixed" block. Exemplary mixed blocks can include, but are not limited to, random blocks, tapered blocks, stepwise blocks, or any other type of mixed block.

A mixed block is "tapered" when both (a) the mole fraction of conjugated diene units in a first section of the block is higher than the mole fraction of conjugated diene units in a second section of the block, wherein the second section of the block is closer to a given end of the block, and (b) condition (a) is true for substantially all sections of the block. Depending on the size of the sections being considered, condition (a) may not be true for all sections, but if so, will be not true at no more than about the level expected by chance.

A mixed block is "random" when the mole fractions of conjugated diene units and monovinylarene units in a section of the block are substantially the same as the mole fractions of conjugated diene units and monovinylarene units in the entire block. This does not preclude the possibility of sections of the block having regularity (i.e., appearing non-random), but such regular sections will typically be present at no more than about the level expected by chance.

Although any methods and materials similar or equivalent to those described herein can be used in the practice or testing of the invention, the typical methods and materials are herein described.

All publications and patents mentioned herein are incorporated herein, in their entirety, by reference for the purpose of describing and disclosing, for example, the constructs and methodologies that are described in the publications, which might be used in connection with the presently described invention.

Applicants disclose several types of ranges in the present invention. When Applicants disclose or claim a range of any type, Applicants' intent is to disclose or claim individually each possible number that such a range could reasonably encompass, including end points of the range as well as any sub-ranges and combinations of sub-ranges encompassed therein. A representative example follows for the kink resistance of tubing produced from block copolymers in embodiments of this invention. For example, by a disclosure that the kink resistance is in a range from about 10 mm to about 25 mm, Applicants intend to recite that the kink resistance can be any kink resistance in the range and can be equal to, for instance, about 10, about 11, about 12, about 13, about 14, about 15, about 16, about 17, about 18, about 19, about 20, about 21, about 22, about 23, about 24, or about 25 mm. Additionally, the kink resistance can be within any range from about 10 to about 25 mm (for example, the kink resistance can be in a range from about 10 to about 20 mm), and this also includes any combination(s) of ranges between about 10 and about 25 mm. Likewise, all other ranges disclosed herein should be interpreted in a manner similar to this representative example.

DETAILED DESCRIPTION OF THE INVENTION

The present disclosure is directed generally to new conjugated diene monovinylarene block copolymers with an internal conjugated diene block, methods for making these block copolymers, and articles produced using these block copolymers. Unexpectedly, the kink resistance and other characteristics of these block copolymers make them suitable to replace flexible PVC in many end-use applications.
Conjugated Diene Monovinylarene Block Copolymers Some embodiments of this invention are directed to conjugated diene monovinylarene block copolymers which can comprise from about 35 phm to about 75 phm monovinylarene monomer, and further, can comprise polymer chains containing a block structure having formula IA or formula IB:

  (IA); or

  (IB).

In formula IA and IB, $S_1$ can be a monoblock of the monovinylarene monomer, wherein $S_1$ can be from about 15 phm to about 45 phm of the copolymer; $B_1$ can be a first monoblock of the conjugated diene monomer, wherein $B_1$ can be from about 0.5 phm to about 10 phm of the copolymer; $(S/B)_1$ can be a mixed block of the conjugated diene monomer and the monovinylarene monomer, wherein the monovinylarene monomer content can be from about 30 wt. % to about 80 wt. %, based on the total weight of $(S/B)_1$; $(S/B)_2$ can be a mixed block of the conjugated diene monomer and the monovinylarene monomer, wherein the conjugated diene monomer content can be from about 70 wt. % to about 99 wt. %, based on the total weight of $(S/B)_2$; and $B_2$ can be a second monoblock of the conjugated diene monomer, wherein $B_2$ can be from about 8 phm to about 30 phm of the copolymer. The abbreviation "phm" means parts by weight per hundred parts of total monomer in the copolymer. The block copolymer also can have a kink resistance of tubing produced from the copolymer of less than or equal to about 32 mm, determined using the test method described herein.

Generally, the features of any of these copolymers (e.g., the phm monovinylarene content in the copolymer, the block structure having formula IA and IB, the phm monovinylarene content in $S_1$, the phm conjugated diene content in $B_1$, the monovinylarene monomer content in $(S/B)_1$, the conjugated diene monomer content in $(S/B)_2$, the phm conjugated diene content in $B_2$, and the kink resistance of the copolymer, among others) are independently described herein, and these features can be combined in any combination to further describe the disclosed copolymers.

Consistent with certain embodiments of this invention, the monovinylarene monomer content of the conjugated diene monovinylarene block copolymers disclosed herein often can be in a range from about 46 phm to about 72 phm, from about 50 phm to about 70 phm, or from about 52 phm to about 68 phm. In further embodiments, the monovinylarene monomer content, based on the conjugated diene monovinylarene block copolymer, can be in a range from about 54 phm to about 68 phm, from about 56 phm to about 66 phm, or from about 57 phm to about 64 phm.

In an embodiment, $S_1$ (the monoblock of the monovinylarene monomer) can be in a range from about 15 phm to about 43 phm, from about 20 phm to about 45 phm, or from about 25 phm to about 40 phm. In another embodiment, $S_1$, based on the conjugated diene monovinylarene block copolymer, can be in a range from about 25 phm to about 38 phm, from about 28 phm to about 38 phm, or from about 30 phm to about 36 phm.

In an embodiment, $B_1$ (the internal monoblock of the conjugated diene monomer) can be in a range from about 1 phm to about 10 phm, from about 2 phm to about 10 phm, or from about 3 phm to about 10 phm. In another embodiment, $B_1$, based on the conjugated diene monovinylarene block copolymer, can be in a range from about 2 phm to about 8 phm, from about 3 phm to about 8 phm, or from about 3 phm to about 7 phm.

In an embodiment, the monovinylarene monomer content in $(S/B)_1$ often can be in a range from about 40 wt. % to about 80 wt. %, from about 40 wt. % to about 75 wt. %, or from about 40 wt. % to about 70 wt. %. In another embodiment, the monovinylarene monomer, based on the weight of $(S/B)_1$, can be in a range from about 40 wt. % to about 65 wt. %, from about 50 wt. % to about 70 wt. %, from about 50 wt. % to about 65 wt. %, or from about 50 wt. % to about 60 wt. %.

In an embodiment, the conjugated diene monomer content in $(S/B)_2$ often can be in a range from about 70 wt. % to about 98 wt. %, from about 75 wt. % to about 98 wt. %, or from about 75 wt. % to about 95 wt. %. In another embodiment, the conjugated diene monomer, based on the weight of $(S/B)_2$, can be in a range from about 72 wt. % to about 95 wt. %, from about 72 wt. % to about 90 wt. %, or from about 82 wt. % to about 92 wt. %.

In an embodiment, $B_2$ (the terminal monoblock of the conjugated diene monomer) can be in a range from about 10 phm to about 30 phm, from about 10 phm to about 25 phm, from about 11 phm to about 25 phm, from about 11 phm to about 22 phm, from about 12 phm to about 22 phm, or from about 13 phm to about 21 phm. In another embodiment, $B_2$, based on the conjugated diene monovinylarene block copolymer, can be in a range from about 13 phm to about 23 phm, from about 14 phm to about 20 phm, or from about 15 phm to about 19 phm.

An illustrative and non-limiting example of a conjugated diene monovinylarene block copolymer of the present invention can have formula IA and the following characteristics: a monovinylarene monomer content in a range from about 54 phm to about 68 phm, $S_1$ in a range from about 28 phm to about 38 phm, $B_1$ in a range from about 2 phm to about 8 phm, a monovinylarene monomer content in $(S/B)_1$ in a range from about 50 wt. % to about 65 wt. %, and a conjugated diene monomer content in $(S/B)_2$ in a range from about 75 wt. % to about 95 wt. %. Another illustrative and non-limiting example of a conjugated diene monovinylarene block copolymer of the present invention can have formula IA and the following characteristics: a monovinylarene monomer content in a range from about 56 phm to about 66 phm, $S_1$ in a range from about 30 phm to about 36 phm, $B_1$ in a range from about 3 phm to about 7 phm, a monovinylarene monomer content in $(S/B)_1$ in a range from about 50 wt. % to about 60 wt. %, and a conjugated diene monomer content in $(S/B)_2$ in a range from about 82 wt. % to about 92 wt. %.

An illustrative and non-limiting example of a conjugated diene monovinylarene block copolymer of the present invention can have formula IB and the following characteristics: a monovinylarene monomer content in a range from about 54 phm to about 68 phm, $S_1$ in a range from about 28 phm to about 38 phm, $B_1$ in a range from about 2 phm to about 8 phm, a monovinylarene monomer content in $(S/B)_1$ in a range from about 50 wt. % to about 65 wt. %, and $B_2$ in a range from about 14 phm to about 20 phm. Another illustrative and non-limiting example of a conjugated diene monovinylarene block copolymer of the present invention can have formula IB and the following characteristics: a monovinylarene monomer content in a range from about 56 phm to about 66 phm, $S_1$ in a range from about 30 phm to about 36 phm, $B_1$ in a range from about 3 phm to about 7 phm, a monovinylarene monomer content in $(S/B)_1$ in a range from about 50 wt. % to about 60 wt. %, and $B_2$ in a range from about 15 phm to about 19 phm.

As noted herein, $S_1$ in formula IA and formula IB can be a monoblock of the monovinylarene monomer, wherein $S_1$ can be from about 15 phm to about 45 phm of the copolymer. In these and other embodiments, $S_1$ can be a single monoblock of the monovinylarene monomer, or $S_1$ can be two or more monoblocks of the monovinylarene monomer. Accordingly, $S_1$ can be produced by a process comprising any suitable number of monovinylarene monomer charges to result in 15 phm to 45 phm, for example, from 1 to 10 charges, from 1 to 6 charges, from 1 to 3 charges, 1 charge, from 2 to 8 charges, from 2 to 5 charges, from 2 to 3 charges, 2 charges, and the like.

As noted herein, $(S/B)_1$ and $(S/B)_2$ can be, respectively, a mixed block of the conjugated diene monomer and the monovinylarene monomer. Any suitable type of mixed block can be used for $(S/B)_1$ and $(S/B)_2$. In one embodiment, for instance, at least one of $(S/B)_1$ and $(S/B)_2$ can be a tapered mixed block, while in another embodiment, at least one of $(S/B)_1$ and $(S/B)_2$ can be a random mixed block. Such mixed blocks can be produced by any suitable technique. As an example, at least one of $(S/B)_1$ and $(S/B)_2$ can be produced by a process comprising dual monomer charges. Additionally or alternatively, at least one of $(S/B)_1$ and $(S/B)_2$ can be produced by a process comprising pulsed monomer charges.

Conjugated diene monovinylarene block copolymers contemplated herein can comprise polymer chains containing a block structure having formula IA, and in certain embodiments, the copolymer can further comprise polymer chains containing a block structure having formula IIA:

$$S_2-B_1-(S/B)_1-(S/B)_2 \quad \text{(IIA)}.$$

Likewise, conjugated diene monovinylarene block copolymers contemplated herein can comprise polymer chains containing a block structure having formula IB, and in certain embodiments, the copolymer can further comprise polymer chains containing a block structure having formula IIB:

$$S_2-B_1-(S/B)_1-B_2 \quad \text{(IIB)}.$$

In formula IIA and formula IIB, $S_2$ can be a monoblock of the monovinylarene monomer, wherein $S_2$ can be from about 5 phm to about 30 phm of the copolymer. In an embodiment, $S_2$ (the monoblock of the monovinylarene monomer in formula IIA and formula BB) can be in a range from about 5 phm to about 25 phm, from about 7 phm to about 30 phm, or from about 7 phm to about 28 phm. In another embodiment, $S_2$, based on the conjugated diene monovinylarene block copolymer, can be in a range from about 10 phm to about 25 phm, from about 12 phm to about 25 phm, from about 14 phm to about 24 phm, from about 14 phm to about 22 phm, or from about 14 phm to about 20 phm.

Like $S_1$ in formula IA and formula IB, $S_2$ in formula IIA and formula IIB can be a single monoblock of the monovinylarene monomer, or $S_2$ can be two or more monoblocks of the monovinylarene monomer. Hence, $S_2$ can be produced by a process comprising any suitable number of monovinylarene monomer charges to result in 5 phm to 30 phm, for example, from 1 to 10 charges, from 1 to 5 charges, from 1 to 3 charges, 1 charge, and the like.

As would be readily recognized by those of skill in the art, polymer chains containing a block structure having formula IA and polymer chains containing a block structure having formula IIA can result from a first charge of an initiator and styrene monomer, a second charge of initiator and styrene monomer, a first charge of butadiene monomer, a mixed charge of styrene and butadiene $(S/B)_1$, and a mixed charge of styrene and butadiene $(S/B)_2$. $S_1$ in formula IA encompasses the styrene blocks from the first two charges, while $S_2$ in formula IIA encompasses the styrene block from the second charge.

Likewise, as would be readily recognized by those of skill in the art, polymer chains containing a block structure having formula IB and polymer chains containing a block structure having formula IIB can result from a first charge of an initiator and styrene monomer, a second charge of initiator and styrene monomer, a first charge of butadiene monomer, a mixed charge of styrene and butadiene $(S/B)_1$, and a second charge of butadiene monomer. $S_1$ in formula IB encompasses the styrene blocks from the first two charges, while $S_2$ in formula IIB encompasses the styrene block from the second charge.

Additionally, as would be readily recognized by those of skill in the art, such a composition can be achieved by blending two or more separately prepared polymers, respectively, having polymer chains of formula IA (or formula IB) and polymer chains of formula IIA (or formula JIB).

In formulas IA, IB, IIA, and IIB, $(S/B)_1$ can be a mixed block of the conjugated diene monomer and the monovinylarene monomer, wherein the monovinylarene monomer content can be from about 30 wt. % to about 80 wt. %, based on the total weight of $(S/B)_1$. Yet, in some embodiments, $(S/B)_1$ can be two mixed blocks of the conjugated diene monomer and the monovinylarene monomer having formula III:

$$—(S/B)_{1A}—(S/B)_{1B}— \quad\quad (III).$$

In formula III, the monovinylarene monomer content in $(S/B)_{1A}$ can be from about 30 wt. % to about 80 wt. %, and the monovinylarene monomer content in $(S/B)_{1B}$ can be from about 30 wt. % to about 80 wt. %. In some embodiments, the monovinylarene monomer content in $(S/B)_{1A}$ often can be in a range from about 40 wt. % to about 80 wt. %, from about 40 wt. % to about 70 wt. %, from about 40 wt. % to about 60 wt. %, from about 45 wt. % to about 65 wt. %, or from about 45 wt. % to about 60 wt. %. Likewise, but independently, the monovinylarene monomer content in $(S/B)_{1B}$ often can be in a range from about 40 wt. % to about 80 wt. %, from about 35 wt. % to about 65 wt. %, from about 45 wt. % to about 70 wt. %, or from about 50 wt. % to about 65 wt. %.

Respectively, $(S/B)_{1A}$ and $(S/B)_{1B}$ can be a mixed block of the conjugated diene monomer and the monovinylarene monomer. Any suitable type of mixed block can be used for $(S/B)_{1A}$ and $(S/B)_{1B}$. In one embodiment, for instance, at least one of $(S/B)_{1A}$ and $(S/B)_{1B}$ can be a tapered mixed block, while in another embodiment, at least one of $(S/B)_{1A}$ and $(S/B)_{1B}$ can be a random mixed block. Such mixed blocks can be produced by any suitable technique. As an example, at least one of $(S/B)_{1A}$ and $(S/B)_{1B}$ can be produced by a process comprising dual monomer charges. Additionally or alternatively, at least one of $(S/B)_{1A}$ and $(S/B)_{1B}$ can be produced by a process comprising pulsed monomer charges.

In an embodiment of this invention, the conjugated diene monovinylarene block copolymer can be an uncoupled conjugated diene monovinylarene block copolymer. Uncoupled block copolymers often can be referred to in the art as terminated or quenched copolymers. In further embodiments, the conjugated diene monovinylarene block copolymer can be an uncoupled unimodal conjugated diene monovinylarene block copolymer, or alternatively, the block copolymer can be an uncoupled multimodal conjugated diene monovinylarene block copolymer.

In yet another embodiment of this invention, the conjugated diene monovinylarene block copolymer can be a coupled conjugated diene monovinylarene block copolymer. Further, the coupled conjugated diene monovinylarene block copolymer can be a coupled unimodal conjugated diene monovinylarene block copolymer or a coupled multimodal conjugated diene monovinylarene block copolymer. In some embodiments, the block copolymer can be produced by coupling at least two different living polymer chains having been produced by at least two separate charges of initiator. Coupling can be accomplished by any method known to those of skill in the art.

In an embodiment, the conjugated diene monovinylarene block copolymer can comprise at least 3 blocks, or alternatively, at least 4 blocks, or at least 5 blocks. For example, the conjugated diene monovinylarene block copolymer can comprise from 3 to 10 blocks, from 4 to 7 blocks, or from 4 to 5 blocks, and so forth. Any blocks in addition to those specified in the formulas for block structures described hereinabove can be selected from any combination of conjugated diene monoblocks, monovinylarene monoblocks, or conjugated diene monovinylarene mixed blocks. Any additional mixed block, for instance, independently can be a tapered mixed block or a random mixed block.

Optionally, the conjugated diene monovinylarene block copolymer can be hydrogenated, although this is not a requirement. In one embodiment, for instance, the block copolymer can be partially hydrogenated, while in another embodiment, the block copolymer can be fully hydrogenated.

Various monovinylarene monomers and conjugated diene monomers can be used to form suitable conjugated diene monovinylarene block copolymers. As described herein, the monovinylarene monomer often can contain from 8 to 18 carbon atoms (e.g., the monovinylarene monomer can be styrene or methylstyrene), and the conjugated diene monomer can contain from 4 to 12 carbon atoms (e.g., the conjugated diene can be isoprene or 1,3-butadiene). Accordingly, in a particular embodiment disclosed herein, the conjugated diene monovinylarene block copolymer can comprise a styrene butadiene block copolymer (SBC).

The block copolymers can be produced using any suitable polymerization process using various types of polymerization reactors, polymerization reactor systems, and polymerization reaction conditions, as recognized by those of skill in the art. While not being limited thereto, general information on processes for producing conjugated diene monovinylarene block copolymers that can be employed in various embodiments of this invention are described in U.S. Pat. Nos. 3,639,517, 6,096,828, 6,420,486, 6,444,755, 6,835,778, 7,037,980, 7,193,014, 7,875,678, 8,415,429, and 8,933,171, the disclosures of which are incorporated herein by reference in their entirety; and U.S. Patent Publication Nos. 2006/0089457 and 2007/0173605, the disclosures of which are incorporated herein by reference in their entirety.

An illustrative process for producing certain block copolymers described herein can comprise contacting:

(i) a first initiator charge and a first charge of the monovinylarene monomer and allowing polymerization to occur until minimal free monomer is present; thereafter contacting all products of step (i) with (ii) a second initiator charge and a second charge of the monovinylarene monomer and allowing polymerization to occur until minimal free monomer is present; thereafter contacting all products of step (ii) with (iii) a first charge of the conjugated diene monomer and allowing polymerization to occur until minimal free monomer is present; thereafter contacting all products of step (iii) with (iv) a first mixture of the monovinylarene monomer and the conjugated diene monomer and allowing polymerization to occur until minimal free monomer is present; thereafter contacting all products of step (iv) with (v) a second mixture of the monovinylarene monomer and the conjugated diene monomer and allowing polymerization to occur until minimal free monomer is present; thereafter contacting all products of step (v) with (vi) a third mixture of the monovinylarene monomer and the conjugated diene monomer and allowing polymerization to occur until minimal free monomer is present; thereafter contacting all products of step (vi) with (vii) a coupling agent.

Another illustrative process for producing certain block copolymers described herein can comprise contacting:

(i) a first initiator charge and a first charge of the monovinylarene monomer and allowing polymerization to occur until minimal free monomer is present; thereafter contacting all products of step (i) with (ii) a second initiator charge and a second charge of the monovinylarene monomer and allowing polymerization to occur until minimal free monomer is present; thereafter contacting all products of step (ii) with (iii) a first charge of the conjugated diene monomer and allowing polymerization to occur until minimal free monomer is present; thereafter contacting all products of step (iii) with (iv) a first mixture of the monovinylarene monomer and the conjugated diene monomer and allowing polymerization to occur until minimal free monomer is present; thereafter contacting all products of step (iv) with (v) a second mixture of the monovinylarene monomer and the conjugated diene monomer and allowing polymerization to occur until minimal free monomer is present; thereafter contacting all products of step (v) with (vi) a second charge of the conjugated diene monomer and allowing polymerization to occur until minimal free monomer is present; thereafter contacting all products of step (vi) with (vii) a coupling agent.

In these processes, and optionally, at least one step in the processes can comprise polymerization in the presence of a modifier. In these and other embodiments, the modifier can comprise any suitable modifier, typically a polar organic compound, non-limiting examples of which can include a potassium alkoxide, a sodium alkoxide, a metal alkoxide or phenolate, a tertiary amine, an ether (e.g., THF, diglyme, etc.), a thioether, and the like, as well as a mixture or combination thereof. In a particular embodiment, the modifier can comprise dimethyl ether, diethyl ether, ethyl methyl ether, ethyl propyl ether, di-n-propyl ether, di-n-octyl ether, anisole, dioxane, 1,2-dimethoxyethane, 1,2-diethoxypropane, dibenzyl ether, diphenyl ether, 1,2-dimethoxybenzene, tetrahydrofuran (THF), potassium tert-amylate (KTA), dimethyl sulfide, diethyl sulfide, di-n-propyl sulfide, di-n-butyl sulfide, methyl ethyl sulfide, dimethylethylamine, tri-n-ethylamine, tri-n-propylamine, tri-n-butylamine, trimethylamine, triethylamine, tetramethylethylenediamine, tetraethylethylenediamine, N,N-di-methylaniline, N-methyl-N-ethylaniline, N-methylmorpholine, and the like, as well as mixtures or combinations thereof. When present, the modifier (e.g., THF) often can be utilized at a molar ratio of the modifier to total monomer of less than about 1:30, less than about 1:50, less than about 1:100, or less than about 1:500. Representative non-limiting ranges for the modifier:monomer molar ratio can include from about 1:100,000 to about 1:50, from about 1:10,000 to about 1:500, from about 1:10,000 to about 1:500, or from about 1:5,000 to about 1:500, and the like.

As described herein, the processes for producing block copolymers are conducted in the presence of an initiator. Suitable initiators are well known to those of skill in the art, such as alkali metal hydrocarbons, a representative example of which is n-butyl lithium. Each initiator can be either the same or different; for instance, the second initiator charge can be the same as or different from the first charge. The amount of initiator employed can depend on many factors, but typically can be in the range from about 0.01 phm to about 1 phm, or from about 0.01 phm to about 0.5 phm, or from about 0.01 phm to about 0.2 phm (phm is parts by weight per hundred parts of total monomer in the copolymer). In a further embodiment, an additional initiator charge can be used in at least one of steps (iii) to (vi), such as, an additional initiator charge in step (iii); additionally or alternatively, an additional initiator charge in step (iv); additionally or alternatively, an additional initiator charge in step (v); or additionally or alternatively, an additional initiator charge in step (vi).

As would be readily recognized by those of skill in the art, the steps in these processes can produce block copolymers with polymer chains containing a block structure having formula IA or formula IB, formula IIA or formula IIB, and/or formula III.

The polymerization process can be conducted in any suitable hydrocarbon diluent at any suitable polymerization temperature, such as in the range of from about −10° C. to about 150° C., or from about 10° C. to about 125° C., at a pressure sufficient to maintain the reaction mixture substantially in the liquid phase. Illustrative hydrocarbon diluents can include, but are not limited to, pentane, hexane, octane, cyclopentane, cyclohexane, and the like, as well as mixtures or combinations thereof. Often, the polymerization process can be conducted in the substantial absence of oxygen and water, and more often, under an inert gas atmosphere. Moreover, as noted herein, each charge of monomer or mixture of monomers can be polymerized to substantial completion, before a subsequent charge of monomer or mixture of monomers (with or without initiator) is commenced.

In step (vii), after polymerization is complete, a coupling agent can be added. Suitable coupling agents can include di- or multivinylarene compounds, di- or multiepoxides, di- or multiisocyanates, di- or multiimines, di- or multialdehydes, di- or multiketones, alkoxytin compounds, di- or multihalides (e.g., dimethyl silicon dichloride, other silicon halides, and halosilanes), mono-, di-, or multianhydrides, di- or multiesters (e.g., esters of monoalcohols with polycarboxylic acids, esters of monohydric alcohols with dicarboxylic acids, esters of monobasic acids with polyalcohols such as glycerol), and the like, and as well as any mixture or combination thereof. Other suitable multifunctional coupling agents can include epoxidized natural source oils, such as epoxidized soybean oil, epoxidized linseed oil, and the like, as well as combinations thereof. The amount of the coupling agent employed can depend on many factors, but typically can be in the range from about 0.1 phm to about 20 phm, from about 0.1 phm to about 5 phm, or from about 0.1 phm to about 2 phm.

Whether coupling or not, the termination of the polymerization reaction can be accomplished using any suitable deactivating agent, illustrative examples of which can include water, carbon dioxide, an alcohol, a phenol, a mono- or di-carboxylic acid, and the like, and combinations thereof.

Block Copolymer Properties, Compositions, and Articles

The conjugated diene monovinylarene block copolymers described herein have an unexpected combination of properties which make them suitable for end-use applications not typically considered for such block copolymers. For instance, these block copolymers can replace flexible PVC in certain end-use applications, such as tubing. These block copolymers also can have any of the polymer properties listed below and in any combination. Moreover, the use of an internal conjugated diene block, instead of a mixed block, may reduce cost and simplify the polymerization process used to produce the conjugated diene monovinylarene block copolymer.

Often, the block copolymer can have a kink resistance of tubing produced from the copolymer of less than or equal to about 32 mm, tested in accordance with DIN EN 13868 as described herein. In one embodiment, the kink resistance can be less than or equal to about 30 mm, less than or equal to about 28 mm, or less than or equal to about 24 mm. Representative non-limiting ranges for the kink resistance include the following: from about 8 to about 32 mm, from about 8 to about 30 mm, from about 8 to about 26 mm, from about 8 to about 24 mm, from about 8 to about 20 mm, from about 9 to about 20 mm, from about 10 to about 32 mm, from about 10 to about 28 mm, from about 10 to about 25 mm, from about 10 to about 22 mm, or from about 10 to about 20 mm, and the like.

Likewise and unexpectedly, the block copolymer also can have a re-kink resistance of tubing produced from the copolymer of less than or equal to about 32 mm, less than or equal to about 30 mm, less than or equal to about 28 mm, or less than or equal to about 26 mm. Similarly, representative non-limiting ranges for the re-kink resistance include the following: from about 8 mm to about 32 mm, from about 8 to about 30 mm, from about 8 mm to about 26 mm, from about 8 to about 24 mm, from about 8 to about 20 mm, from about 10 to about 30 mm, from about 10 mm to about 28 mm, from about 12 to about 28 mm, or from about 12 to about 25 mm, and the like. The re-kink resistance is tested in accordance with DIN EN 13868 as described herein.

Block copolymers in various embodiments of this invention generally can have a melt flow rate (MFR) of less than or equal to about 25 g/10 min. MFR is determined in accordance with ASTM D1238-13 at 200° C. with a 5 Kg load. Melt flow rates in the range from about 2 to about 25, from about 3 to about 20, from about 4 to about 20, or from about 5 to about 15 g/10 min, are contemplated in embodiments of this invention. For example, the block copolymer can have a MFR in a range from about 2 to about 20, from about 3 to about 18, or from about 3 to about 12 g/10 min.

The Shore A hardness of the block copolymer typically can fall within a range from about 20 to about 95, from about 35 to about 90, or from about 40 to about 90. Other suitable and non-limiting ranges for the Shore A hardness include from about 50 to about 95, from about 50 to about 90, from about 60 to about 90, from about 65 to about 90, from about 65 to about 85, from about 70 to about 85, from about 72 to about 86, and the like.

Given the flexibility and relative softness of the block copolymers disclosed herein, blocking of the resin pellets of the copolymer can be a concern. In embodiments of this invention, the copolymer can have a pellet blocking force—equipment and test procedure are described hereinbelow—of less than or equal to about 120 $lb_f$, less than or equal to about 115 $lb_f$, less than or equal to about 110 $lb_f$, or less than or equal to about 100 $lb_f$. The lower limit of the blocking force is generally not determined (i.e., free flowing pellets).

While not required, the block copolymers described herein typically do not contain a plasticizer. Indeed, this can be an advantage over other polymers, such as PVC, which may require relatively large amounts of plasticizers to impart flexibility. However, if desired for a particular end-use, a plasticizer can be combined with the block copolymer at an appropriate loading.

The block copolymer can be modified with any suitable additive or additives, as recognized by those of skill in the art. For instance, the copolymer can be modified with one or more additives selected from an antioxidant, an acid scavenger, an antiblock additive, a slip additive (e.g., a fatty acid amide, erucamide), a colorant, a filler, a polymer processing aid (e.g., a fluoroelastomer), a UV absorber, a UV inhibitor, a lubricant (e.g., a wax, a mineral oil), and the like, as well as any combination thereof. In some embodiments, the copolymer can further comprise an antioxidant; alternatively, an acid scavenger; alternatively, an antiblock additive; alternatively, a slip additive; alternatively, a colorant; alternatively, a filler; alternatively, a polymer processing aid; alternatively, a UV absorber; alternatively, a UV inhibitor; or alternatively, a lubricant. These and other suitable additives and modifiers, which may be added to the copolymers in order to provide beneficial polymer processing or end-use product attributes, are described in *Modern Plastics Encyclopedia*, Mid-November 1995 Issue, Vol. 72, No. 12; and *Film Extrusion Manual—Process, Materials, Properties*, TAPPI Press, 1992; the disclosures of which are incorporated herein by reference in their entirety.

Blends or combinations of the block copolymers and another polymer also are encompassed herein. For instance, the second polymer can be a different conjugated diene monovinylarene block copolymer, a styrenic polymer (e.g., a styrene butadiene polymer, a polystyrene, a high impact polystyrene, etc.), or a rubber (a polybutadiene, a polyisoprene, a poly-2-chloro-1,3-butadiene, a poly-1-chloro-1,3-butadiene, an ethylene/propylene terpolymer, a butadiene/acrylonitrile copolymer, a butyl rubber, an acrylic rubber, a styrene/isobutylene/butadiene copolymer, an isoprene/acrylic ester copolymer, etc.), as well as combinations thereof. Other polymer types can be used as blend components as well, such as polyolefins (LDPE, LLDPE, PP, etc.), ethylene/vinyl acetate, and so forth. Additionally, a composition containing the block copolymer of this invention and a second polymer also can contain one or more suitable additives or modifiers, such as those described hereinabove. Multilayer structures (e.g., coextrusions) and/or laminated structures (e.g., adhesive laminations) also can contain the block copolymer, whether as a single layer or in a blend, and with any additives or modifiers suitable for the end-use application of the multilayer or laminated structure.

The block copolymers, blends, multilayer and laminated structures, and so forth, can be formed into various articles of manufacture, and these articles of manufacture can have any thickness suitable for the desired end-use application. Articles which can comprise block copolymers, compositions, multilayer structures, etc., of this invention can include, but are not limited to, a film, a sheet, a bottle or container, a fiber or fabric, an adhesive or coating, a medical device or material, a pipe, or a flexible tube, and the like. Various processes can be employed to form these articles. Non-limiting examples of these processes include injection molding, blow molding, rotational molding, film extrusion, sheet extrusion, profile extrusion, thermoforming, and the like. Such processes and materials are described in *Modern Plastics Encyclopedia*, Mid-November 1995 Issue, Vol. 72, No. 12; and *Film Extrusion Manual—Process, Materials, Properties*, TAPPI Press, 1992. In some embodiments of this invention, an article of manufacture can comprise any of the block copolymers described herein (e.g., including blends, compositions, multilayer structures, etc.), can have any of the copolymer properties described herein, and the article of manufacture can be a tubing product, such as flexible tubing for medical applications.

EXAMPLES

The invention is further illustrated by the following examples, which are not to be construed in any way as imposing limitations to the scope of this invention. Various other aspects, embodiments, modifications, and equivalents thereof which, after reading the description herein, may suggest themselves to one of ordinary skill in the art without departing from the spirit of the present invention or the scope of the appended claims.

Kink resistance testing was performed with an apparatus designed and built in accordance with DIN EN 13868: 2002-11 (Annex A, short term test method), and as described herein. The water line consisted of ⅜-inch (9.525-mm) OD (outside diameter) tubing with flow meters to measure water flow. The groove used to hold the tubing test specimen in place had a depth of 5.05 mm as measured. Tubing test specimens were 16 inches (406.4 mm) in length, and the test speed was kept low enough to avoid over pressurizing the tubing.

The tubing test specimens had an OD of ¼ inch (6.35 mm), represented by d in the equation below, and a nominal ID (inside diameter) of ⅛ inch (3.175 mm). In reference to the testing diagram in FIG. 1, the plate distance was measured as D in mm, and the reported kink resistance (C in the equation below, mm) was calculated according to the following equation:

$$C=D+2h-d(\sqrt{2}-1)=D+7.5 \text{(mm)},$$

where D is the measured plate distance at half of the original water flow rate (decrease in flow rate such that the initial flow rate through the straight tubing is reduced by 50%), h is the measured groove depth (5.05 mm), and d is the tubing OD (6.35 mm). A manual press capable of providing a force up to 50 $lb_f$ was used to close the gap between plates during testing.

The water temperature was set to ambient conditions of about 25° C. The rate at which force was applied by the press was manually adjusted to prevent sudden kinking of the tubing during the test (i.e., to prevent the water flow rate from decreasing to zero before the kink resistance could be measured).

Re-kink resistance was measured under the same conditions as those described for kink resistance testing. After the initial kink test was performed, the re-kink resistance was measured by opening the plate distance and repeating the procedure to measure the point at which the water flow rate decreased to half of the flow rate observed at the start of the re-kink test. Typically, the re-kink measurement (C in the equation provided above) was higher than the kink measurement due to the weak spot that formed in the tubing during the original kink measurement.

Shore A hardness testing was performed according to ASTM D2240-05 with a 30 second delay. The Shore A hardness test was performed at ambient conditions on a compression molded 2 inch×2 inch (50.8 mm×50.8 mm) square specimen with ½ inch (12.7 mm) thickness.

Melt Flow Rate (MFR) was measured according to modified ASTM D1238-13 using the standard polystyrene conditions (load of 5 kg and temperature of 200° C.) with a holding time of 300 seconds.

Pellet blocking force was measured as the shear force required to break a cylindrically-shaped pellet aggregate. To form the pellet aggregate, about 300 grams of pellets were placed in a 3 inch (76.2 mm) ID rigid pipe, a 2.5 kg weight was placed on top of the pellets, and the cylinder and its contents were placed in a forced air oven maintained at 65° C. for 90 hours. After cooling to room temperature, the weight and cylinder were removed, then the pellet aggregate was placed in a shearing fixture in an Instron® load frame, and tested in shear. The pellet blocking force (anti-blocking property) of the sample was the pound force ($lb_f$) required to shear the pellet aggregate.

The following pre-made tubing samples were obtained and used for comparative testing.

1. Tygon® 1: chemical resistant clear PVC tubing—commercially available from McMaster-Carr (Catalog #5231K144).
2. Tygon® 2: formulation 2375, ultra high chemical resistant PVC tubing—commercially available from McMaster-Carr (Catalog #5103K32).
3. C-Flex® 50A: thermoplastic elastomer tubing—commercially available from Cole-Parmer.

The following polymer resins were converted into tubing, and the resulting tubing was used for comparative testing.

4. Vector® 8508 SBS block copolymer—commercially available from Dexco Polymers LP—nominal 29 wt. % styrene.
5. Styroflex® 2G66 SB block copolymer—commercially available from Styrolution.
6. Versaflex™ HC MT224 thermoplastic elastomer—commercially available from GLS Thermoplastic Elastomers PolyOne Corp—blend of SEBS and PP.
7. Medalist® MD-575 thermoplastic elastomer—commercially available from Teknor Apex—blend of SEBS and PP.
8. C-Flex® (Lab): Tubing was produced from pellets obtained by chopping thermoplastic elastomer C-Flex® 50A Tubing into pieces—tubing commercially available from Cole-Parmer.
9. K-Resin® SBC XK40—commercially available from Chevron Phillips Chemical Company LP—nominal 76 wt. % styrene.
10. K-Resin® SBC KR20—commercially available from Chevron Phillips Chemical Company LP—nominal 62 wt. % styrene.

Examples 4-10 were converted to tubing using single screw extrusion. The extruder was a Vented Extruder Model 2523, ¾", L/D 25:1 Ratio, from C. W. Brabender® Instruments Inc. The tubing die was an interchangeable die head with 0.25 inch (6.35 mm) OD and 0.125 inch (3.175 mm) ID mandrel tip combinations. The typical temperature profile ranges used for tubing extrusion are provided in Table I below.

TABLE I

Extrusion Conditions.

| | Range | Range |
|---|---|---|
| Rear (feed) | 280°-365° F. | (138°-185° C.) |
| Middle (transition) | 320°-390° F. | (160°-199° C.) |
| Front (near die end) | 320°-390° F. | (160°-199° C.) |
| Die | 280°-365° F. | (138°-185° C.) |
| Extruder speed | 40-100 RPM | |
| Puller Speed | 15-40 RPM | |

Examples 1-10

As shown in Table II, the tubing samples of Examples 1-3 had acceptable kink resistance, re-kink resistance, and Shore A hardness. The tubing of Example 8 was produced from pellets obtained by chopping the C-Flex® 50A tubing of Example 3 into pieces, and extruding the pieces into tubing using the extrusion system and conditions described above. Example 8 also had acceptable kink resistance, re-kink resistance, and Shore A hardness, and had basically the same properties as that of Example 3. The tubing samples of Examples 4 and 9-10 showed poor kink resistance and, therefore, would not be suitable to replace flexible PVC in medical tubing applications. The Shore A hardness of Example 5 was too high for consideration as a PVC replacement in certain applications.

Examples 11-18

The materials and polymerization processes for Examples 11-18 are as described below. Cyclohexane was dried over activated alumina and stored under nitrogen. n-Butyl lithium initiator (abbreviated BuLi) was used as received at 2 wt. % in cyclohexane. THF was stored over activated alumina under nitrogen. Styrene (S) and butadiene (B) were purified over activated alumina. Epoxidized soybean oil was a 20% solution in $C_6$ purged with and stored under $N_2$.

The polymerizations were performed in a 2-gallon stainless steel reactor using sequential solution polymerization under nitrogen. The reactor was equipped with a jacket for temperature control, a double auger impeller, and baffles. Generally, each block was formed by polymerizing the monomer or mixture of monomers from which the desired units of the block are derived.

Cyclohexane was initially charged to the reactor, followed by THF (0.05 phm). The temperature was adjusted to about 60° C., and the BuLi initiator was charged, followed by the first charge of styrene monomer (Styrene 1). The second charge contained BuLi and a second charge of styrene monomer (Styrene 2). The third charge contained butadiene monomer (Butadiene 1). The next two charges were mixed charges of butadiene and styrene (B2+S3, B3+S4) at specified weight percentages of the butadiene (Bd %). The last charge was a mixed charge of butadiene and styrene (B4+S5) at a specified weight percentage of the butadiene (Bd %), or a monoblock of butadiene (B4). Feed lines to the reactor were flushed with about 0.1 kg cyclohexane following each charge. Polymerization was allowed to continue to completion after each monomer or monomer mixture charge. The polymerization temperature ranged from about 38° C. to about 120° C., and pressure ranged from about 2 psig to about 180 psig. Following completion of the sequential polymerizations, a coupling agent (CA, epoxidized soybean oil) was charged to the reactor, and reacted at about 100° C. for about 15 min. After coupling, the reaction was terminated by adding about 0.2 phm water and adding $CO_2$.

Table III summarizes certain production parameters (e.g., charge sequence, composition of each charge) and properties of Examples 11-18. Tubing specimens of Examples 11-18 were produced from the SBC block copolymers via the extrusion system and conditions described above.

As shown in Table III, Examples 11-15 had polymer chains containing an internal butadiene block (Butadiene 1) after two styrene blocks (Styrene 1 and Styrene 2), whereas Examples 16-18 did not contain the butadiene monoblock. While Examples 16-18 demonstrated a good balance of properties desirable for tubing applications (low kink resistance, low re-kink resistance, low pellet blocking force, and acceptable Shore A hardness), Examples 11-15—which contained an internal butadiene monoblock—unexpectedly had equivalent or superior kink resistance and re-kink resistance, while maintaining both acceptable pellet blocking force and Shore A hardness. Moreover, the overall good balance of properties desired for tubing applications could be achieved in Examples 11-15 regardless of whether the polymer (prior to coupling) had a terminal mixed block (B4/S5) or a terminal butadiene block (B4).

TABLE II

Comparative Examples 1-10.

| Example No. | 1 | 2 | 3 | 4 | 5 | 6 | 7 | 8 | 9 | 10 |
|---|---|---|---|---|---|---|---|---|---|---|
| Nominal Styrene (phm) | N/T | N/T | N/T | 29 | N/T | N/T | N/T | N/T | 76 | 62 |
| MFR (g/10 min) | N/T | N/T | N/T | 12* | N/T | N/T | N/T | 75 | 10 | 6 |
| Kink Resistance (mm) | 23 | 26 | 21 | 35 | 13 | 21 | 23 | 26 | XX | XX |
| Re-Kink Resistance (mm) | 25 | 27 | 24 | 35 | 18 | 24 | 25 | 27 | XX | XX |
| Shore A Hardness | 60 | 66 | 50 | 66 | 84 | 71 | 78 | 51 | 93 | 90 |
| Pellet Blocking ($lb_f$) | N/T | N/T | N/T | 50 | 12 | 4.4 | 7.0 | N/T | 29 | 18 |

Notes:
XX = Too rigid for kink resistance test;
N/T = Not Tested;
Examples 1-3 were commercial tubing samples, while Examples 4-10 were produced using tubing extrusion as described above;
*data provided is from a product data sheet.

TABLE III

Examples 11-18.

| Example | 11 | 12 | 13 | 14 | 15 | 16 | 17 | 18 |
|---|---|---|---|---|---|---|---|---|
| BuLi, phm | 0.060 | 0.057 | 0.057 | 0.057 | 0.057 | 0.057 | 0.065 | 0.065 |
| THF, phm | 0.05 | 0.05 | 0.05 | 0.05 | 0.05 | 0.05 | 0.05 | 0.05 |
| Styrene 1, phm | 17 | 17 | 15 | 15 | 15 | 15 | 17 | 17 |
| BuLi, phm | 0.055 | 0.052 | 0.052 | 0.052 | 0.052 | 0.052 | 0.06 | 0.06 |
| Styrene 2, phm | 16 | 16 | 17 | 17 | 17 | 17 | 16 | 16 |
| Butadiene 1, phm | 4 | 6 | 4 | 6 | 4 | 0 | 0 | 0 |
| B2 + S3, phm | 22 | 20 | 22 | 20 | 22 | 26 | 26 | 26 |
| Bd % in (B2/S3) | 50 | 45 | 50 | 45 | 50 | 58 | 54 | 54 |
| B3 + S4, phm | 24 | 24 | 25 | 25 | 25 | 25 | 24 | 24 |
| Bd % in (B3/S4) | 38 | 38 | 40 | 40 | 40 | 40 | 38 | 38 |

TABLE III-continued

Examples 11-18.

| Example | 11 | 12 | 13 | 14 | 15 | 16 | 17 | 18 |
|---|---|---|---|---|---|---|---|---|
| B4 + S5 or B4, phm | 17 | 17 | 17 | 17 | 17 | 17 | 17 | 17 |
| Bd % in (B4/S5 or B4) | 88 | 88 | 88 | 88 | 100 | 88 | 88 | 100 |
| CA, phm | 0.4 | 0.4 | 0.4 | 0.4 | 0.4 | 0.4 | 0.4 | 0.4 |
| Total Styrene, phm | 63 | 63 | 62 | 62 | 58 | 62 | 62 | 60 |
| Kink Resistance (mm) | 16 | 11 | 14 | 14 | 17 | 14 | 20 | 18 |
| Re-Kink Resistance (mm) | 18 | 18 | 17 | 18 | 21 | 18 | 22 | 20 |
| Shore A Hardness | 76 | 81 | 76 | 76 | 79 | 80 | 72 | 74 |
| MFI (g/10 min) | 10.0 | 7.2 | 7.6 | 7.6 | 4.1 | 8.0 | 3.9 | 3.0 |
| Pellet Blocking (lb$_f$) | 93 | 48 | 70 | 108 | 110 | 70 | 66 | 51 |

The invention is described above with reference to numerous aspects and embodiments, and specific examples. Many variations will suggest themselves to those skilled in the art in light of the above detailed description. All such obvious variations are within the full intended scope of the appended claims. Other embodiments of the invention can include, but are not limited to, the following (embodiments are described as "comprising" but, alternatively, can "consist essentially of" or "consist of"):

Embodiment 1

A conjugated diene monovinylarene block copolymer comprising from about 35 phm to about 75 phm monovinylarene monomer, and comprising polymer chains containing a block structure having formula IA or formula IB:

$$S_1—B_1—(S/B)_1—(S/B)_2 \quad \text{(IA); or}$$

$$S_1—B_1—(S/B)_1—B_2 \quad \text{(IB); wherein:}$$

$S_1$ is a monoblock of the monovinylarene monomer, wherein $S_1$ is from about 15 phm to about 45 phm of the copolymer;

$B_1$ is a first monoblock of the conjugated diene monomer, wherein $B_1$ is from about 0.5 phm to about 10 phm of the copolymer;

$(S/B)_1$ is a mixed block of the conjugated diene monomer and the monovinylarene monomer, wherein the monovinylarene monomer content is from about 30 wt. % to about 80 wt. %, based on the total weight of $(S/B)_1$;

$(S/B)_2$ is a mixed block of the conjugated diene monomer and the monovinylarene monomer, wherein the conjugated diene monomer content is from about 70 wt. % to about 99 wt. %, based on the total weight of $(S/B)_2$; and $B_2$ is a second monoblock of the conjugated diene monomer, wherein $B_2$ is from about 8 phm to about 30 phm of the copolymer; and wherein a kink resistance of tubing produced from the copolymer and tested in accordance with DIN EN 13868 is less than or equal to about 32 mm.

Embodiment 2. The copolymer defined in embodiment 1, wherein the monovinylarene monomer contains from 8 to 18 carbon atoms.

Embodiment 3. The copolymer defined in embodiment 1 or 2, wherein the monovinylarene monomer is styrene.

Embodiment 4. The copolymer defined in any one of embodiments 1-3, wherein the conjugated diene monomer contains from 4 to 12 carbon atoms.

Embodiment 5. The copolymer defined in any one of embodiments 1-4, wherein the conjugated diene monomer is a butadiene.

Embodiment 6. The copolymer defined in any one of embodiments 1-5, wherein the conjugated diene monomer is 1,3-butadiene.

Embodiment 7. The copolymer defined in any one of embodiments 1-6, wherein the conjugated diene monovinylarene block copolymer is a styrene butadiene block copolymer.

Embodiment 8. The copolymer defined in any one of embodiments 1-7, wherein $S_1$ is in any range disclosed herein, e.g., from about 20 phm to about 45 phm, from about 25 phm to about 40 phm, from about 28 phm to about 38 phm, from about 30 phm to about 36 phm, etc.

Embodiment 9. The copolymer defined in any one of embodiments 1-8, wherein $B_1$ is in any range disclosed herein, e.g., from about 1 phm to about 10 phm, from about 2 phm to about 10 phm, from about 2 phm to about 8 phm, from about 3 phm to about 7 phm, etc.

Embodiment 10. The copolymer defined in any one of embodiments 1-9, wherein the monovinylarene monomer content in $(S/B)_1$ is in any range disclosed herein, e.g., from about 40 wt. % to about 80 wt. %, from about 40 wt. % to about 70 wt. %, from about 50 wt. % to about 65 wt. %, from about 50 wt. % to about 60 wt. %, etc., based on $(S/B)_1$.

Embodiment 11. The copolymer defined in any one of embodiments 1-10, wherein the conjugated diene monomer content in $(S/B)_2$ is in any weight percentage range disclosed herein, e.g., from about 75 wt. % to about 95 wt. %, from about 72 wt. % to about 90 wt. %, from about 82 wt. % to about 92 wt. %, etc., based on $(S/B)_2$.

Embodiment 12. The copolymer defined in any one of embodiments 1-10, wherein $B_2$ is in any range disclosed herein, e.g., from about 10 phm to about 25 phm, from about 11 phm to about 25 phm, from about 12 phm to about 22 phm, from about 14 phm to about 20 phm, from about 15 phm to about 19 phm, etc., of the copolymer.

Embodiment 13. The copolymer defined in any one of embodiments 1-12, wherein the copolymer comprises monovinylarene monomer in any range disclosed herein, e.g., from about 46 phm to about 72 phm, from about 52 phm to about 68 phm, from about 54 phm to about 68 phm, from about 56 phm to about 66 phm, from about 57 phm to about 64 phm, etc., based on the weight of the copolymer.

Embodiment 14. The copolymer defined in any one of embodiments 1-13, wherein:

the monovinylarene monomer is from about 54 phm to about 68 phm of the copolymer;

$S_1$ is from about 28 phm to about 38 phm of the copolymer;

$B_1$ is from about 2 phm to about 8 phm of the copolymer;

the monovinylarene monomer content in $(S/B)_1$ is from about 50 wt. % to about 65 wt. % of $(S/B)_1$; and the conjugated diene monomer content in $(S/B)_2$ is from about 75 wt. % to about 95 wt. % of $(S/B)_2$.

Embodiment 15. The copolymer defined in any one of embodiments 1-13, wherein:

the monovinylarene monomer is from about 54 phm to about 68 phm of the copolymer;

$S_1$ is from about 28 phm to about 38 phm of the copolymer;

$B_1$ is from about 2 phm to about 8 phm of the copolymer;

the monovinylarene monomer content in $(S/B)_1$ is from about 50 wt. % to about 65 wt. % of $(S/B)_1$; and $B_2$ is from about 14 phm to about 20 phm of the copolymer.

Embodiment 16. The copolymer defined in any one of embodiments 1-15, wherein $S_1$ is two or more monoblocks of the monovinylarene monomer.

Embodiment 17. The copolymer defined in any one of embodiments 1-16, wherein $S_1$ is produced by a process comprising any number of monovinylarene monomer charges disclosed herein, e.g., from 1 to 10 charges, from 2 to 5 charges, 2 charges, etc.

Embodiment 18. The copolymer defined in any one of embodiments 1-17, wherein at least one of $(S/B)_1$ and $(S/B)_2$ is a tapered mixed block.

Embodiment 19. The copolymer defined in any one of embodiments 1-18, wherein at least one of $(S/B)_1$ and $(S/B)_2$ is a random mixed block.

Embodiment 20. The copolymer defined in any one of embodiments 1-19, wherein at least one of $(S/B)_1$ and $(S/B)_2$ is produced by a process comprising dual monomer charges.

Embodiment 21. The copolymer defined in any one of embodiments 1-20, wherein at least one of $(S/B)_1$ and $(S/B)_2$ is produced by a process comprising pulsed monomer charges.

Embodiment 22. The copolymer defined in any one of embodiments 1-19, wherein the copolymer further comprises polymer chains containing a block structure having formula IIA or formula IIB:

$S_2$—$B_1$—$(S/B)_1$—$(S/B)_2$     (IIA); or

$S_2$—$B_1$—$(S/B)_1$—$B_2$     (IIB); wherein:

$S_2$ is a monoblock of the monovinylarene monomer, wherein $S_2$ is from about 5 phm to about 30 phm of the copolymer.

Embodiment 23. The copolymer defined in embodiment 22, wherein $S_2$ is in any range disclosed herein, e.g., from about 5 phm to about 25 phm, from about 12 phm to about 25 phm, from about 14 phm to about 24 phm, from about 14 phm to about 20 phm, etc.

Embodiment 24. The copolymer defined in any one of embodiments 22-23, wherein $S_2$ is produced by a process comprising any number of monovinylarene monomer charges disclosed herein, e.g., from 1 to 10 charges, from 1 to 5 charges, 1 charge, etc.

Embodiment 25. The copolymer defined in any one of embodiments 1-24, wherein $(S/B)_1$ is two mixed blocks of the conjugated diene monomer and the monovinylarene monomer having formula III:

—$(S/B)_{1A}$—$(S/B)_{1B}$—     (III); wherein:

the monovinylarene monomer content in $(S/B)_{1A}$ is from about 30 wt. % to about 80 wt. % of $(S/B)_{1A}$, and the monovinylarene monomer content in $(S/B)_{1B}$ is from about 30 wt. % to about 80 wt. % of $(S/B)_{1B}$.

Embodiment 26. The copolymer defined in embodiment 25, wherein the monovinylarene monomer content in $(S/B)_{1A}$ is in any weight percentage range disclosed herein, e.g., from about 40 wt. % to about 80 wt. %, from about 40 wt. % to about 60 wt. %, from about 45 wt. % to about 65 wt. %, from about 45 wt. % to about 60 wt. %, etc., based on $(S/B)_{1A}$.

Embodiment 27. The copolymer defined in any one of embodiments 25-26, wherein the monovinylarene monomer content in $(S/B)_{1B}$ is in any weight percentage range disclosed herein, e.g., from about 40 wt. % to about 80 wt. %, from about 35 wt. % to about 65 wt. %, from about 45 wt. % to about 70 wt. %, from about 50 wt. % to about 65 wt. %, etc., based on $(S/B)_{1B}$.

Embodiment 28. The copolymer defined in any one of embodiments 25-27, wherein at least one of $(S/B)_{1A}$ and $(S/B)_{1B}$ is a tapered mixed block.

Embodiment 29. The copolymer defined in any one of embodiments 25-28, wherein at least one of $(S/B)_{1A}$ and $(S/B)_{1B}$ is a random mixed block.

Embodiment 30. The copolymer defined in any one of embodiments 25-29, wherein at least one of $(S/B)_{1A}$ and $(S/B)_{1B}$ is produced by a process comprising dual monomer charges.

Embodiment 31. The copolymer defined in any one of embodiments 25-30, wherein at least one of $(S/B)_{1A}$ and $(S/B)_{1B}$ is produced by a process comprising pulsed monomer charges.

Embodiment 32. The copolymer defined in any one of embodiments 1-31, wherein the copolymer is produced by a process comprising coupling the polymer chains with any coupling agent disclosed herein, e.g., dimethyl silicon dichloride, an epoxidized soy bean oil, etc.

Embodiment 33. The copolymer defined in any one of embodiments 1-32, wherein the copolymer is a coupled copolymer.

Embodiment 34. The copolymer defined in any one of embodiments 1-33, wherein the copolymer is a multimodal copolymer.

Embodiment 35. The copolymer defined in any one of embodiments 1-34, wherein the copolymer is fully hydrogenated.

Embodiment 36. The copolymer defined in any one of embodiments 1-34, wherein the copolymer is partially hydrogenated.

Embodiment 37. The copolymer defined in any one of embodiments 1-36, wherein the copolymer has a melt flow rate in any range disclosed herein, e.g., from about 2 to about 20, from about 3 to about 18, from about 3 to about 12 g/10 min, etc.

Embodiment 38. The copolymer defined in any one of embodiments 1-37, further comprising any additive disclosed herein, e.g., an antioxidant, an acid scavenger, an antiblock additive, a slip additive, a colorant, a filler, a polymer processing aid, a UV inhibitor, a lubricant, etc., or any combination thereof.

Embodiment 39. The copolymer defined in any one of embodiments 1-38, wherein the copolymer does not contain a plasticizer.

Embodiment 40. The copolymer defined in any one of embodiments 1-39, wherein the kink resistance is in any range disclosed herein, e.g., less than or equal to about 30 mm, from about 8 mm to about 32 mm, from about 8 to about 24 mm, from about 10 mm to about 25 mm, from about 9 mm to about 20 mm, etc.

Embodiment 41. The copolymer defined in any one of embodiments 1-40, wherein the tubing has a re-kink resistance in any range disclosed herein, e.g., less than or equal to about 32 mm, from about 8 mm to about 32 mm, from about 10 to about 30 mm, from about 12 mm to about 25 mm, etc.

Embodiment 42. The copolymer defined in any one of embodiments 1-41, wherein the copolymer has a Shore A hardness in any range disclosed herein, e.g., from about 20 to about 95, from about 60 to about 90, from about 65 to about 85, from about 70 to about 85, from about 72 to about 86, etc.

Embodiment 43. The copolymer defined in any one of embodiments 1-42, wherein the copolymer has a pellet blocking force in any range disclosed herein, e.g., less than or equal to about 120 $lb_f$, less than or equal to about 115 $lb_f$, less than or equal to about 110 $lb_f$, etc.

Embodiment 44. A composition comprising the copolymer defined in any one of embodiments 1-43 and a second polymer, e.g., a styrene butadiene polymer, a polystyrene, a high impact polystyrene, a polybutadiene, a polyolefin, etc., or any combination thereof.

Embodiment 45. A composition comprising the copolymer defined in any one of embodiments 1-43, a second polymer, and an additive.

Embodiment 46. An article comprising the copolymer or composition defined in any one of embodiments 1-45.

Embodiment 47. An article comprising the copolymer or composition defined in any one of embodiments 1-45, wherein the article is a film, a medical device or material, or an adhesive.

Embodiment 48. A tubing product comprising the copolymer or composition, e.g., prepared from the copolymer or composition, defined in any one of embodiments 1-45.

Embodiment 49. A process for producing the copolymer defined in any one of embodiments 1-43, the process comprising contacting:

(i) a first initiator charge and a first charge of the monovinylarene monomer and allowing polymerization to occur until minimal free monomer is present; thereafter contacting all products of step (i) with (ii) a second initiator charge and a second charge of the monovinylarene monomer and allowing polymerization to occur until minimal free monomer is present; thereafter contacting all products of step (ii) with (iii) a first charge of the conjugated diene monomer and allowing polymerization to occur until minimal free monomer is present; thereafter contacting all products of step (iii) with (iv) a first mixture of the monovinylarene monomer and the conjugated diene monomer and allowing polymerization to occur until minimal free monomer is present; thereafter contacting all products of step (iv) with (v) a second mixture of the monovinylarene monomer and the conjugated diene monomer and allowing polymerization to occur until minimal free monomer is present; thereafter contacting all products of step (v) with (vi) a third mixture of the monovinylarene monomer and the conjugated diene monomer and allowing polymerization to occur until minimal free monomer is present; thereafter contacting all products of step (vi) with (vii) a coupling agent.

Embodiment 50. A process for producing the copolymer defined in any one of embodiments 1-43, the process comprising contacting:

(i) a first initiator charge and a first charge of the monovinylarene monomer and allowing polymerization to occur until minimal free monomer is present; thereafter contacting all products of step (i) with (ii) a second initiator charge and a second charge of the monovinylarene monomer and allowing polymerization to occur until minimal free monomer is present; thereafter contacting all products of step (ii) with (iii) a first charge of the conjugated diene monomer and allowing polymerization to occur until minimal free monomer is present; thereafter contacting all products of step (iii) with (iv) a first mixture of the monovinylarene monomer and the conjugated diene monomer and allowing polymerization to occur until minimal free monomer is present; thereafter contacting all products of step (iv) with (v) a second mixture of the monovinylarene monomer and the conjugated diene monomer and allowing polymerization to occur until minimal free monomer is present; thereafter contacting all products of step (v) with (vi) a second charge of the conjugated diene monomer and allowing polymerization to occur until minimal free monomer is present; thereafter contacting all products of step (vi) with (vii) a coupling agent.

Embodiment 51. The process defined in embodiment 49 or 50, wherein at least one step in the process comprises polymerization in the presence of a modifier.

Embodiment 52. The process defined in embodiment 51, wherein the modifier comprises any modifier disclosed herein, e.g., a potassium alkoxide, a sodium alkoxide, a metal alkoxide or phenolate, a tertiary amine, an ether, etc., as well as any combination thereof.

Embodiment 53. The process defined in embodiment 51 or 52, wherein the modifier comprises THF.

Embodiment 54. The process defined in any one of embodiments 51-53, wherein the modifier is present at any molar ratio of modifier to total monomer disclosed herein, e.g., less than about 1:50, less than about 1:30, from about 1:100,000 to about 1:50, from about 1:10,000 to about 1:500, etc.

Embodiment 55. The process defined in any one of embodiments 49-54, wherein an additional initiator charge is used in at least one of steps (iii) to (vi).

We claim:

1. A conjugated diene monovinylarene block copolymer comprising from about 54 phm to about 68 phm monovinylarene monomer, and comprising polymer chains containing a block structure having formula IA:

$$S_1\text{—}B_1\text{—}(S/B)_1\text{—}(S/B)_2 \qquad (IA);$$

wherein:

$S_1$ is a monoblock of the monovinylarene monomer, wherein $S_1$ is from about 28 phm to about 38 phm of the copolymer;

$B_1$ is a first monoblock of the conjugated diene monomer, wherein $B_1$ is from about 2 phm to about 8 phm of the copolymer;

$(S/B)_1$ is a mixed block of the conjugated diene monomer and the monovinylarene monomer, wherein the monovinylarene monomer content is from about 50 wt. % to about 65 wt. %, based on the total weight of $(S/B)_1$; and $(S/B)_2$ is a mixed block of the conjugated diene monomer and the monovinylarene monomer, wherein the conjugated diene monomer content is from about 75 wt. % to about 95 wt. %, based on the total weight of $(S/B)_2$; and wherein a kink resistance of tubing produced from the copolymer and tested in accordance with DIN EN 13868 is less than or equal to about 32 mm.

2. The copolymer of claim 1, wherein:

$S_1$ is in a range from about 30 phm to about 36 phm; and $B_1$ is in a range from about 3 phm to about 7 phm.

3. The copolymer of claim 1, wherein the copolymer comprises monovinylarene monomer in a range from about 56 phm to about 66 phm.

4. The copolymer of claim 1, wherein:
the monovinylarene monomer is styrene;
the conjugated diene monomer is a butadiene; and
the kink resistance is in a range from about 8 to about 24 mm.

5. The copolymer of claim 1, wherein the copolymer is a styrene butadiene block copolymer.

6. The copolymer of claim 1, wherein
the conjugated diene monomer content in $(S/B)_2$ is in a range from about 82 wt. % to about 92 wt. %, based on $(S/B)_2$.

7. The copolymer of claim 1, wherein $S_1$ is two or more monoblocks of the monovinylarene monomer.

8. The copolymer of claim 1, wherein the copolymer further comprises polymer chains containing a block structure having formula IIA:

$$S_2\text{—}B_1\text{—}(S/B)_1\text{—}(S/B)_2 \qquad (IIA);$$

wherein:
$S_2$ is a monoblock of the monovinylarene monomer, wherein $S_2$ is from about 14 phm to about 20 phm of the copolymer.

9. The copolymer of claim 1, wherein $(S/B)_1$ is two mixed blocks of the conjugated diene monomer and the monovinylarene monomer having formula III:

$$\text{—}(S/B)_{1A}\text{—}(S/B)_{1B}\text{—} \qquad (III);$$

wherein:
the monovinylarene monomer content in $(S/B)_{1A}$ is from about 30 wt. % to about 80 wt. % of $(S/B)_{1A}$; and the monovinylarene monomer content in $(S/B)_{1B}$ is from about 30 wt. % to about 80 wt. % of $(S/B)_{1B}$.

10. The copolymer of claim 9, wherein the monovinylarene monomer content in $(S/B)_{1A}$ is from about 45 wt. % to about 60 wt. %, and the monovinylarene monomer content in $(S/B)_{1B}$ is from about 50 wt. % to about 65 wt. %.

11. The copolymer of claim 1, wherein the conjugated diene monovinylarene block copolymer is a styrene butadiene block copolymer with a kink resistance in a range from about 8 mm to about 26 mm.

12. The copolymer of claim 11, wherein the copolymer has:
a melt flow rate at 200° C. with a 5 Kg load in a range from about 2 to about 20 g/10 min; and
a Shore A hardness in a range from about 65 to about 90.

13. The copolymer of claim 11, wherein the copolymer has:
a pellet blocking force of less than or equal to about 120 $lb_f$; and
a re-kink resistance in a range from about 12 mm to about 28 mm.

14. An article of manufacture comprising the copolymer of claim 1.

15. A tubing product comprising the copolymer of claim 1.

16. A composition comprising the copolymer of claim 1 and a second polymer.

17. A process to produce a conjugated diene monovinylarene block copolymer comprising from about 35 phm to about 75 phm monovinylarene monomer, and comprising polymer chains containing a block structure having formula IA:

$$S_1\text{—}B_1\text{—}(S/B)_1\text{—}(S/B)_2 \qquad (IA);$$

wherein:
$S_1$ is a monoblock of the monovinylarene monomer, wherein $S_1$ is from about 15 phm to about 45 phm of the copolymer;
$B_1$ is a first monoblock of the conjugated diene monomer, wherein $B_1$ is from about 0.5 phm to about 10 phm of the copolymer;
$(S/B)_1$ is a mixed block of the conjugated diene monomer and the monovinylarene monomer, wherein the monovinylarene monomer content is from about 30 wt. % to about 80 wt. %, based on the total weight of $(S/B)_1$; and
$(S/B)_2$ is a mixed block of the conjugated diene monomer and the monovinylarene monomer, wherein the conjugated diene monomer content is from about 70 wt. % to about 99 wt. %, based on the total weight of $(S/B)_2$; and
wherein a kink resistance of tubing produced from the copolymer and tested in accordance with DIN EN 13868 is less than or equal to about 32 mm;
the process comprising contacting:
(i) a first initiator charge and a first charge of the monovinylarene monomer and allowing polymerization to occur until minimal free monomer is present; thereafter contacting all products of step (i) with
(ii) a second initiator charge and a second charge of the monovinylarene monomer and allowing polymerization to occur until minimal free monomer is present; thereafter contacting all products of step (ii) with
(iii) a first charge of the conjugated diene monomer and allowing polymerization to occur until minimal free monomer is present; thereafter contacting all products of step (iii) with
(iv) a first mixture of the monovinylarene monomer and the conjugated diene monomer and allowing polymerization to occur until minimal free monomer is present; thereafter contacting all products of step (iv) with
(v) a second mixture of the monovinylarene monomer and the conjugated diene monomer and allowing polymerization to occur until minimal free monomer is present; thereafter contacting all products of step (v) with
(vi) a third mixture of the monovinylarene monomer and the conjugated diene monomer and allowing polymerization to occur until minimal free monomer is present; thereafter contacting all products of step (vi) with
(vii) a coupling agent.

18. The process of claim 17, wherein at least one step in the process comprises polymerization in the presence of a modifier, and/or an additional initiator is used in at least one of steps (iii) to (vi).

19. A process to produce a conjugated diene monovinylarene block copolymer comprising from about 35 phm to about 75 phm monovinylarene monomer, and comprising polymer chains containing a block structure having formula IB:

$$S_1\text{—}B_1\text{—}(S/B)_1\text{—}B_2 \qquad (IB);$$

wherein:
$S_1$ is a monoblock of the monovinylarene monomer, wherein $S_1$ is from about 15 phm to about 45 phm of the copolymer;
$B_1$ is a first monoblock of the conjugated diene monomer, wherein $B_1$ is from about 0.5 phm to about 10 phm of the copolymer;
$(S/B)_1$ is a mixed block of the conjugated diene monomer and the monovinylarene monomer, wherein the monovinylarene monomer content is from about 30 wt. % to about 80 wt. %, based on the total weight of $(S/B)_1$; and $B_2$ is a second monoblock of the conjugated diene monomer, wherein $B_2$ is from about 8 phm to about 30 phm of the copolymer; and wherein a kink resistance of tubing produced from the copolymer and tested in accordance with DIN EN 13868 is less than or equal to about 32 mm;

the process comprising contacting:

(i) a first initiator charge and a first charge of the monovinylarene monomer and allowing polymerization to occur until minimal free monomer is present; thereafter contacting all products of step (i) with (ii) a second initiator charge and a second charge of the monovinylarene monomer and allowing polymerization to occur until minimal free monomer is present; thereafter contacting all products of step (ii) with (iii) a first charge of the conjugated diene monomer and allowing polymerization to occur until minimal free monomer is present; thereafter contacting all products of step (iii) with (iv) a first mixture of the monovinylarene monomer and the conjugated diene monomer and allowing polymerization to occur until minimal free monomer is present; thereafter contacting all products of step (iv) with (v) a second mixture of the monovinylarene monomer and the conjugated diene monomer and allowing polymerization to occur until minimal free monomer is present; thereafter contacting all products of step (v) with (vi) a second charge of the conjugated diene monomer and allowing polymerization to occur until minimal free monomer is present; thereafter contacting all products of step (vi) with (vii) a coupling agent.

20. The process of claim 19, wherein at least one step in the process comprises polymerization in the presence of a modifier, and/or an additional initiator is used in at least one of steps (iii) to (vi).

21. A conjugated diene monovinylarene block copolymer comprising from about 54 phm to about 68 phm monovinylarene monomer, and comprising polymer chains containing a block structure having formula IB:

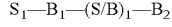

$$S_1-B_1-(S/B)_1-B_2 \quad \text{(IB)};$$

wherein:

$S_1$ is a monoblock of the monovinylarene monomer, wherein $S_1$ is from about 28 phm to about 38 phm of the copolymer;

$B_1$ is a first monoblock of the conjugated diene monomer, wherein $B_1$ is from about 2 phm to about 8 phm of the copolymer;

$(S/B)_1$ is a mixed block of the conjugated diene monomer and the monovinylarene monomer, wherein the monovinylarene monomer content is from about 50 wt. % to about 65 wt. %, based on the total weight of $(S/B)_1$; and $B_2$ is a second monoblock of the conjugated diene monomer, wherein $B_2$ is from about 10 phm to about 25 phm of the copolymer; and wherein a kink resistance of tubing produced from the copolymer and tested in accordance with DIN EN 13868 is less than or equal to about 32 mm.

22. The copolymer of claim 21, wherein:

$B_2$ is from about 12 phm to about 22 phm of the copolymer;

the monovinylarene monomer is styrene;

the conjugated diene monomer is a butadiene; and the kink resistance is in a range from about 8 to about 24 mm.

23. A tubing product comprising the copolymer of claim 22.

24. The copolymer of claim 21, wherein the conjugated diene monovinylarene block copolymer is a styrene butadiene block copolymer with a kink resistance in a range from about 8 mm to about 26 mm.

25. The copolymer of claim 21, wherein:

the copolymer further comprises polymer chains containing a block structure having formula IIB:

$$S_2-B_1-(S/B)_1-B_2 \quad \text{(IIB)};$$

wherein:

$S_2$ is a monoblock of the monovinylarene monomer, wherein $S_2$ is from about 14 phm to about 20 phm of the copolymer; and $(S/B)_1$ is two mixed blocks of the conjugated diene monomer and the monovinylarene monomer having formula III:

$$-(S/B)_{1A}-(S/B)_{1B}- \quad \text{(III)};$$

wherein:

the monovinylarene monomer content in $(S/B)_{1A}$ is from about 30 wt. % to about 80 wt. % of $(S/B)_{1A}$; and the monovinylarene monomer content in $(S/B)_{1B}$ is from about 30 wt. % to about 80 wt. % of $(S/B)_{1B}$.

* * * * *